United States Patent
Nelson et al.

(10) Patent No.: US 10,482,753 B2
(45) Date of Patent: Nov. 19, 2019

(54) INFECTION CONTROL MONITORING SYSTEM

(71) Applicant: Minnesota Imaging and Engineering LLC, Excelsior, MN (US)

(72) Inventors: William Bert Nelson, Excelsior, MN (US); Robert Sigurd Nelson, La Mesa, CA (US); Glenn Albert Nickele, Forest Lake, MN (US)

(73) Assignee: Minnesota Imaging and Engineering LLC, Excelsior, MN (US)

( * ) Notice: Subject to any disclaimer, the term of this patent is extended or adjusted under 35 U.S.C. 154(b) by 20 days.

(21) Appl. No.: 13/987,917

(22) Filed: Sep. 17, 2013

(65) Prior Publication Data

US 2015/0077258 A1   Mar. 19, 2015
US 2019/0279491 A9   Sep. 12, 2019

Related U.S. Application Data

(60) Provisional application No. 61/848,430, filed on Jan. 4, 2013.

(51) Int. Cl.
*G08B 21/24* (2006.01)
*G06Q 30/02* (2012.01)
*G06Q 50/22* (2018.01)
*G08B 21/02* (2006.01)

(52) U.S. Cl.
CPC ....... *G08B 21/245* (2013.01); *G06Q 30/0207* (2013.01); *G06Q 50/22* (2013.01); *G08B 21/02* (2013.01)

(58) Field of Classification Search
CPC ...... G08B 21/245; G08B 21/02; G06Q 50/22; G06Q 30/0207
See application file for complete search history.

(56) References Cited

U.S. PATENT DOCUMENTS

| 8,742,932 B2 * | 6/2014 | Casares | G07C 1/10 222/52 |
|---|---|---|---|
| 2006/0016877 A1 * | 1/2006 | Bonalle et al. | 235/380 |
| 2007/0288263 A1 * | 12/2007 | Rodgers | A61B 5/0002 705/2 |

(Continued)

*Primary Examiner* — Mohamed Barakat
(74) *Attorney, Agent, or Firm* — Dorsey & Whitney LLP (57) ABSTRACT

The invention provides an automated hand hygiene/infection control monitoring sensor-based system suitable for improving hand hygiene and multiple infection control measures and ensuring compliance by health care workers as well as visitors to hospitals and clinics. The use of biometric identification devices such as cameras for face recognition and profiling, microphones for voice recognition, etc. permit highly accurate identification without the use of removable identification devices such as identification badges which may include bar codes, magnetic strips or wireless devices such as RFIDS. Identification badges are removable and hence susceptible to being lost, misplaced, etc. Visitors are typically not assigned identification badges and hence enforcement of hand hygiene policies is minimal. Additional applications include reducing food contamination in food industry, the spread of diseases in schools, in businesses, in corporations and governmental facilities and public access facilities such as public restrooms, dining areas and transportation.

22 Claims, 3 Drawing Sheets

(56) References Cited

U.S. PATENT DOCUMENTS

| | | | |
|---|---|---|---|
| 2008/0099045 A1* | 5/2008 | Glenn et al. | 134/18 |
| 2008/0222963 A1* | 9/2008 | Zwart | 49/503 |
| 2009/0089093 A1* | 4/2009 | Johnson | G06F 19/327 705/2 |
| 2009/0091458 A1* | 4/2009 | Deutsch | G06F 19/327 340/573.1 |
| 2009/0224907 A1* | 9/2009 | Sinha | G08B 21/245 340/539.11 |
| 2010/0134296 A1* | 6/2010 | Hwang | 340/573.1 |
| 2010/0315244 A1 | 12/2010 | Tokhtuev et al. | |
| 2011/0148586 A1* | 6/2011 | Anderson | G06F 19/327 340/10.1 |
| 2011/0297696 A1* | 12/2011 | Casares | G07C 1/10 222/52 |
| 2012/0055986 A1 | 3/2012 | Sahud | |
| 2012/0085006 A1* | 4/2012 | Phillips | 40/541 |
| 2012/0112914 A1* | 5/2012 | Wegelin et al. | 340/573.1 |
| 2012/0249331 A1* | 10/2012 | Wegelin et al. | 340/573.1 |
| 2012/0261593 A1* | 10/2012 | Noori | 250/492.1 |
| 2012/0307109 A1* | 12/2012 | Morioka | G11B 27/034 348/231.3 |
| 2013/0122807 A1* | 5/2013 | Tenarvitz | H04B 5/0031 455/41.1 |
| 2013/0229276 A1* | 9/2013 | Hunter | G08B 21/245 340/501 |

\* cited by examiner

INFECTION CONTROL MONITORING SYSTEM

This is a continuation of the provisional application Ser. No. 61/848,430 filed on Jan. 4, 2013.

FIELD OF THE INVENTION

This invention describes an automated hand hygiene/infection control monitoring sensor-based system suitable for improving hand hygiene and multiple infection control measures and ensuring compliance by health care workers as well as visitors to hospitals and clinics. Additional applications include reducing food contamination in food industry, the spread of diseases in schools, in businesses, in corporations and governmental agencies as well as lessening the risk of infection amongst the public via commonly used public restrooms, dining areas, transportation, etc.

BACKGROUND OF THE INVENTION

Hand hygiene (such as hand washing) is a simple but highly effective method for controlling the spread of infectious diseases in a health care setting, in food preparation settings, as well as any area (public or private) where multiple persons access a common restroom or have physical contact with common tools, equipment etc. Compliance by individuals, despite the prolific use of warning signs and admonitions from authorities or peers has always been problematic. Current automated compliance systems rely on identification means such as RFID tags in hospital employee identification badges (including bracelets, etc.) or other portable wireless identification devices for tracking. The use of removable employee identification which incorporates RFID tags or other wireless identification devices has a limitation in that the identification device can be removed (misplaced, left with other clothes, left in the car, used by a different person, etc.) Notably, in hospitals, convincing visitors to wash their hands has had very limited success due to the implication that the hospital must be unclean. Current RFID-based, automated compliance systems used in hospitals do not effectively address the issue of visitors and hand hygiene such as hand washing.

SUMMARY OF THE INVENTION

The invention utilizes developments in tracking and identification software and hardware to implement an automated hand hygiene/infection control monitoring sensor-based system to improve hand hygiene and multiple infection control measures and ensure compliance for all individuals entering the monitored environments. Additional benefits may include a reduction in criminal acts committed by employees and/or visitors. This invention offers a monitoring system that can be employed in order to encourage greater compliance rates in utilizing infection control techniques (most notably hand hygiene techniques such as hand washing) in various settings, using facial recognition (and/or other identification techniques) to track and verify individuals. The monitoring system can be comprised of separate components that are electronically linked or the components can be integrated into a single monitoring unit such as a box or other suitable protective container. The monitoring system can be integrated with other sensor devices (for example, video cameras, motion sensors, etc.) already employed to monitor a space. Although a monitoring box can incorporate data processing hardware, software and storage it can also incorporate an electronic communications link (wired or wireless) to a computer for data post-processing, storage, verification and display. The monitoring box or unit is typically mounted on or next to an exit/entry point to the monitored environment or at relevant locations within the monitored environment (for example, next to a sink). It physically incorporates or electronically incorporates (is linked to) one or more of the following tracking and recognition capabilities: a motion detector device (including, but not limited to, acoustic or electromagnetic sensors), an identification device including at least one biometric identification device such as a camera for face recognition and profile (with optional video capability or a separate camera for video), a biometric reader such as a finger print reader (including an infrared finger print reader), palm print reader, a microphone for voice recognition, chemical sensors, etc. Optional non-biometric identification devices may include a wireless electronic identification device such as a wireless RFID reader, a badge reader or scanner, a touch pad, a touch screen, a key board, a virtual keyboard (including an infrared keyboard), etc. Furthermore the monitoring unit incorporates a holographic or conventional display screen (which may have touch screen capability) for visual automated and interactive instructions and a speaker for verbal automated and interactive instructions. In addition, cameras or other recognition devices can be used to recognize gestures (including hand waving); capabilities already incorporated into electronic gaming units (for example, "leap motion"). These input devices permit the individual to lookup information, contact individuals within the hospital, request assistance, request maintenance, enter access codes, by-pass the monitoring unit protocols, enter instructions for personnel, etc.

A dispenser (which can be incorporated into the monitoring unit or be employed as a separate box or container of any desired shape) typically includes a unit filled with disinfectant and/or soap that can be automatically dispensed by a sensor based system if the hands are placed below the sensor device. Additional features such as an UV treatment device for the hands can be incorporated into the dispenser for improved infection control. Optionally, an inspection device can be included with the dispenser in order to evaluate the effectiveness of the cleaning process. Additional types of dispenser units can be used to distribute other infection control materials (equipment) such as gloves, masks, etc.

The individual will have to first look at a camera or scanner in order to implement face recognition and profile acquisition, speak into a microphone for voice recognition, present a hand for a biometric fingerprint or palm print reader, present an eye for an eye scanner, present a face, neck, arm or hand for an infrared imager, etc. Badge swipes and RFID readers can also be employed for additional verification. Upon either verification or registration of the individual the dispenser will dispense the appropriate type of soap or disinfectant from a reservoir with a pre-measured amount of cleaning agent as the hands are placed below the sensor. One or more override mechanisms can be incorporated into the monitoring system. For example, override mechanisms that can be enabled by authorities include a button that can be pushed or a proximity sensor that can be triggered. The monitoring system may also be programmed to accept other override mechanisms such as voice commands (using a microphone) or an electronically transmitted command. For example, if the person has washed their hands at an unmonitored sink, or in emergency medical situations, monitoring can be suspended with this button or with a voice command. The dispenser may be designed with the capability to dispense one or more types of cleaning agents such as soap or other disinfectants (for sensitivity/allergy options). Appropriate soap/disinfectant can be dispensed via placement of hands, voice command or computer programmed preference for any registered individual. If more than one dispensing reservoir is present a signal such as a flashing light and/or audio announcement can be used to indicate the appropriate reservoir. When soap is dispensed, an optional UV light directed towards the hands will also turn on for a pre-determined time to augment hand disinfection. The amount of time spent washing as well as the technique can be monitored providing real time intervention to prescribe corrective measures when the hand washing time and technique is unsatisfactory. Optionally, recordings can be made for review to determine individual and overall compliance.

In situations in which multiple compliance measures are necessary, the system will indicate the level of compliance required, as programmed by authorities, by auditory or visual display instructions that describe the level of infection control active in a particular room (routine/hand wash, respiratory, contact precautions, resp. isolation, enteric precautions, etc.) In a hospital setting, this compliance level is entered into the computer monitoring system when a patient is admitted or when the patient's status or location changes. Once an individual has fulfilled all compliance measures, the monitoring system will inform the individual that he/she may enter (or leave) the room (including any time limits). Auditory and/or visual prompts will indicate any other infection measures which need to be taken prior to entering (or leaving) the room. Respiratory mask dispenser, gown dispenser, glove dispenser and soap dispenser systems can be linked by wired and/or wirelessly communicate with each other and the local computer or a central server to monitor for compliance to all infection control steps. In settings where multiple entrances or exits exist, or where additional hand washing dispensers may be placed in areas away from a doorway, wired and/or wireless communication between dispensers and the local computer or a central server will register compliance if any site is utilized appropriately.

Entrance and exit from a room can be controlled by securing the door as well as by compliance mechanisms such as visual or auditory alerts and/or an incentive-based program that uses rewards or penalties. An incentive-based program can be implemented for employees as well as visitors/the public (for example, a reduced parking fee, cafeteria billing or gift shop billing for a visitor). Thus, an incentive program can be coordinated with other hospital-related services. The incentive program can be used to motivate visitors and employees to participate in the identification process. Employees and/or visitors will be informed that they will be compensated for enrolling in and complying with the hand hygiene program. Implementation of a monitoring system is particularly straightforward if employees or visitors can be identified and registered within the system prior to entering the room. One or more recognition capabilities such as facial recognition (visual, infrared), physical metrics (a profile or physical appearance such as height, hair color, etc.), voice recognition or other biometrics are commonly used in security surveillance as well as customer recognition. By employing this technology one can overcome several limitations of identification badges (which may utilize bar codes, magnetic strips or RFIDs) since identification badges can be removed, misplaced, damaged, etc.). In hospitals, clinics, commercial and public facilities (restaurant, school, factory, etc.) a monitoring system can be used to register employees (and visitors) by recording their relevant identification metrics such as face, physical parameters (profile), voice and other biometric parameters which can be stored in a local database or central database (updated as frequently as is deemed prudent such as instantly, hourly, daily, weekly, etc.). Incentive measures can be implemented to encourage participation. Optionally, prior employees' identification metrics can be retained in the data base.

A monitoring system can be used to register visitors into the data base when they enter the facility at a control point or location or registration can be dispersed (entering a parking lot, at a cafeteria, a gift shop, a pharmacy, a restroom, a waiting room, etc. If an individual can provide a credit card or similar financial tool when registering then the individual's financial transactions can be automated such as parking payments, purchases at the pharmacy, gift shop, cafeteria, vending machines, insurance co-payments, etc. When used only for registration purposes a monitoring system can exclude (or disable) features such as a motion sensor. Registration can be automated or supervised by a trained individual. It is a simple process to use these employee or visitor identification metrics to verify all individuals that enter or leave a compliance monitored environment and request compliance with hand washing or other infection control steps. Implementation of a monitoring system also represents a means to discourage unauthorized individuals from entering the area (thus the hand hygiene system can communicate data such as live video to a facility's security system whether or not the unauthorized individual washes their hands).

DETAILED DESCRIPTION

The invention provides a coordinated monitoring system to improve infection control in a wide variety of environments. Hand washing compliance represents one important application of the monitoring system. Variants of the monitoring system can also be used to track compliance with use of masks, gowns, eye shields, head covers, overalls, hazmat suits or other infection control/safety measures. Real time intervention can be implemented when there is a lack of compliance and corrective measures can be prescribed. Optionally, recordings can be made for review to determine individual and overall compliance. The expected benefits include increased patient, worker and visitor safety in the hospital setting and a decrease in the spread of disease as infection control compliance improves significantly. Furthermore, patient security is enhanced since access to the patient's room can be monitored for registered employees and visitors. In food industry settings a decrease in spread of infection to customers is expected. In private business or corporate settings, a reduction in employee illness and a reduction in sick time can be expected. In school settings, a reduction in instructor as well as student illness and absenteeism can be expected. Monitoring should also enhance security in these settings.

One of the key functions of the monitoring system is its role as a tracking station which can be located at the entrance to or exit from the environment or setting intended to be monitored. This device will communicate using wired or wireless (Wi-Fi, Blue-Tooth, etc.) technology with other similar devices (separate monitoring and dispenser units, combination monitoring/dispensing units) near entry/exit points of that same environment as well as centralized computer servers. The implementation of various wireless technologies will be based on issues such as cost, range and security.

The data acquired by the monitoring system can be analyzed by the utilizing facility for infection control purposes, disease tracking, monitoring individuals, etc. Authorized individuals will be able to customize programming of the units as necessary. For example, in a hospital setting a number of infection control measures may be implemented. (e.g. hand washing, wearing mask, gloves, etc) The required level of compliance will be input into any of the monitoring units by an authorized individual. Monitoring systems can be linked so that updates for multiple monitor units can be executed from a single monitor unit. The level of compliance can be input via verbal command after proper identification of the authorized individual by the monitoring systems. The monitoring system can track compliance by individuals using one or more biometric techniques, including but not limited to, face recognition, finger print recognition, hand recognition, palm recognition, arm recognition, retina recognition, sub-dermal pattern recognition, voice recognition, chemical sensing, object and body recognition, etc. Object and body recognition would identify an individual based on body shape and features (including features obscured by clothing such as gowns and masks). Object and body recognition may also be used to identify if face mask, gown, gloves are being worn and determine whether the attire is appropriate for infection control. In addition, other recognition capabilities (typically used by employees) that can be incorporated into the monitoring system include badges, bracelets, implants, etc. that may use one or more markers such as bar codes, magnetic strips, or RFIDs (or other wireless capabilities). In private settings (hospitals, factories, restaurants, etc), all employees will be registered in a server database and will be assigned levels of authorization to the system.

Visitors can also be registered in the system and assigned a level of authorization. For example, images of a new visitor, including his or her profile and face can be readily acquired when first entering a facility. This data can be processed using face recognition technology and then store on a server. The server can then distribute this information to the appropriate monitor system or systems if facial recognition verification is to be performed locally. Alternatively, facial recognition can be performed at the server when a visitor accesses the monitored room or environment and has his or her image (face, profile) acquired by a monitor system. Yet another hardware and software configuration is for a monitoring system to incorporate the facial recognition conversion hardware and software capability (in place of a separate server).

Motion detectors will track the approach of individuals. This could then prompt an audible alert (alarm or verbal) to the individual to participate in one or more biometric identification processes such as facial recognition, voice recognition, a retinal scan, etc. In addition, the individual may be required to swipe or have a badge read. An audible command as well as visually-displayed written command (both commands are in the registered individual's preferred language) or schematic diagram instruction can then follow to alert subject to wash hands, wear mask, wear gown, etc. Authorized users can also program the server to send out text pages, text messages, or verbal prompts as desired. For example, when Dr Smith approaches Mr Jones' room, a text page to Mr Jones' nurse is sent out and the nurse is made aware. This improves communication and care may be better coordinated. Once an individual is identified, his/her name, status, etc. may be displayed on the viewing screen (for example, an LCD display). ("Dr Jones", "Sue Smith-RN", "Joe Henry-security officer", "Sandy Beech-visitor", etc.) The individual verifies that the identity is correct verbally or by physical gesture (interrupting a beam, using a touch screen, proximity sensor, etc.). Individual will then have limited amount of time (for example, approximately 30 seconds) to trigger the soap/disinfectant dispenser. Infra-red sensor will sense presence of hands below the dispenser and the appropriate aliquot of the preferred soap or disinfectant will be dispensed. In the case of a soap dispenser, if desired, one can program a "countdown clock" to appear on the LCD screen to insure hands are washed for an adequate time period. If hands are removed prematurely from the monitored area, non-compliance is registered. An optional UV light can be employed to illuminate the hands for a set time period after soap/disinfectant is dispensed in order to augment the disinfectant effect. An optional inspection device can be incorporated into the monitor system that examines the hands after washing to evaluate washing effectiveness. Once hands are adequately washed the monitoring system will recognize the individual as being compliant with respect to that aspect of infection control. If further steps are needed (mask, etc) again, another prompt will follow. For more complete tracking, additional items needed may be stored in monitored cabinet which will link up with the other system features for complete compliance tracking. Electronic locking mechanisms on doors could also be set to communicate via a wired or wireless network with monitoring system. Doors can be made to lock or unlock base on compliance status. Door opening mechanisms could also be linked to automatically open doors when compliant. This would avoid using clean hands on potentially contaminated door knobs.

Figure 1:
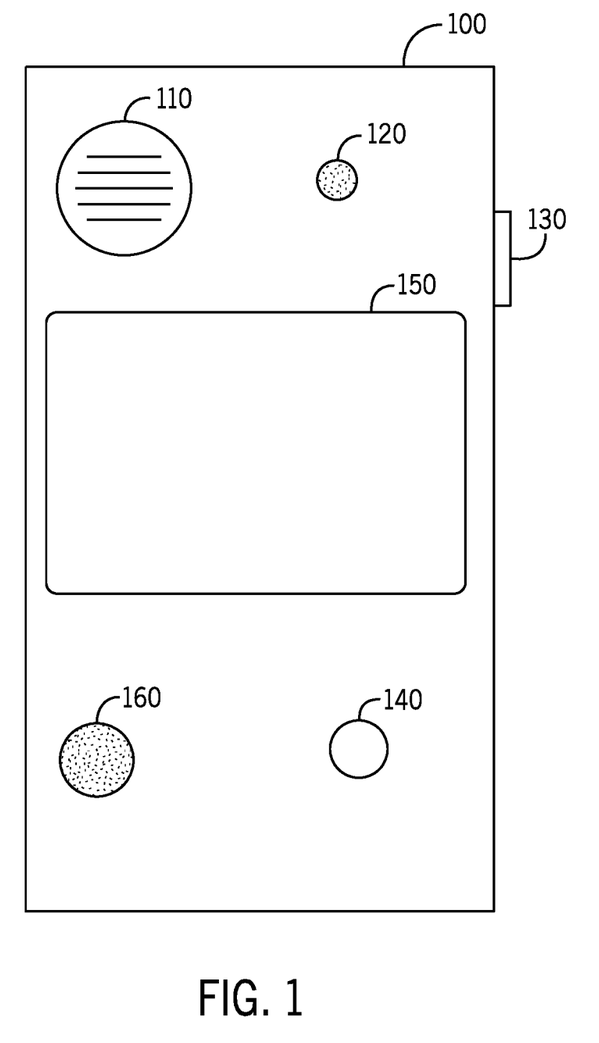
FIG. 1 illustrates a perspective view of a monitoring unit including a speaker and microphone, an optical sensor (camera, scanner, etc.), a wired or wireless communications unit, a motion sensor, a hand wash over-ride button or proximity sensor and a view screen.

The monitor system incorporates one or more of the following tracking and recognition capabilities that can be employed for hygiene and safety compliance: one or motion detectors (including, but not limited to, acoustic, electromagnetic sensors, video sensors), a camera for face recognition, an optional camera to provide video capability (which could be the same as the face recognition camera), a biometric reader (finger, hand, palm, voice, retina, sub-dermal, etc.), an RFID reader, a badge scanner or reader, a microphone for voice recognition, a speaker for automated commands and verbal instructions/information (such as acknowledging the identity of the individual) and interactive communications, chemical sensors, an optional hand washing inspection unit as well as a display screen for visual automated instructions and interactive communications. One or more override devices (a push button, a proximity sensor, a voice command, a touch screen, a virtual keyboard) can be incorporated into the monitoring system. The monitoring system can also be programmed to accept electronic commands that override the system FIG. 1 shows an implementation of a monitoring unit 100 which incorporates a microphone/speaker device 110 for voice commands and voice recognition, a camera 120 for facial recognition and video recording, a wireless Wi-Fi and blue tooth transmitter/receiver device 130 providing Internet and RFID communications, a motion detector device 140, a visual display 150 such as an LCD tough screen and a hand wash override push button or sensor 160. When video recording technology is employed the video recordings can be sent to a central server for storage and review or accessed by a security system as needed. Optionally the video recordings can be retained at the monitor system. Video recording can be prompted by motion detection. Video recording can be performed at fixed or variable frame rates (if data storage space is a consideration). The server may store all videos for review, or random ratio which includes all non-compliant encounters.

Figure 2:
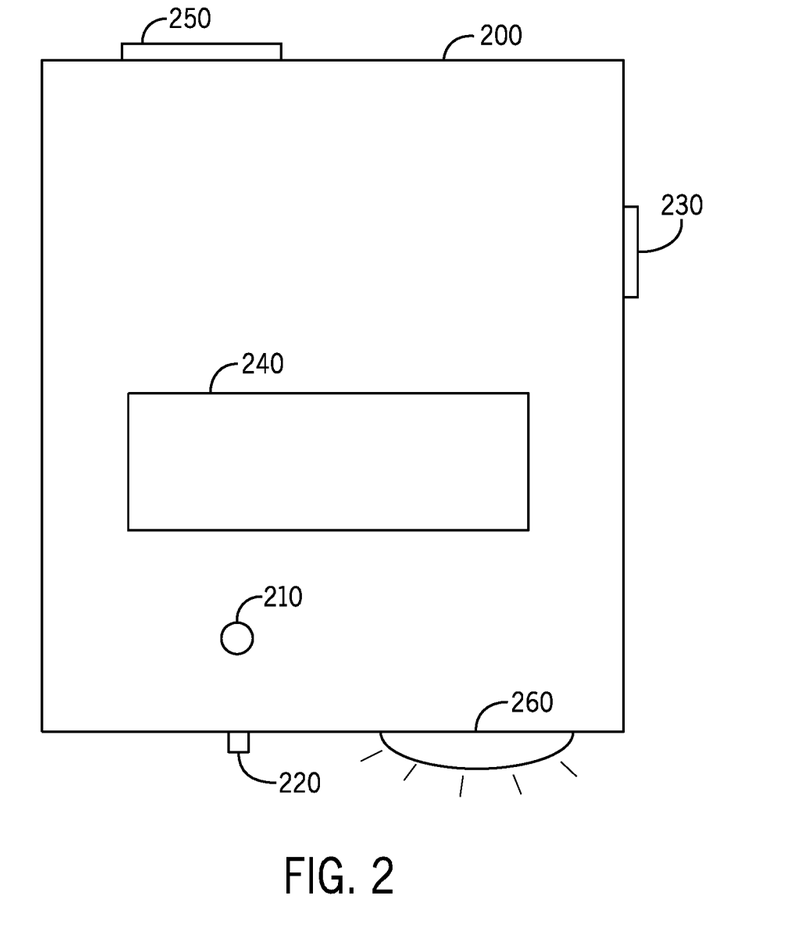
FIG. 2 illustrates a perspective view of soap/sanitizer dispenser including a wired or wireless communications unit linking the dispenser to a monitor unit, a sensor to trigger dispensing of a cleaning agent, a reservoir with a pre-measured amount of cleaning agent and an access door for refilling soaps and sanitizers (cleaning agents).

The monitoring system can link to other monitor systems, soap/disinfectant dispenser (as well as other types of dispensers) and a central server using wired and/or wireless networking. The monitor system can be configured to monitor people entering or leaving a room or setting by different doors. The soap/disinfectant (cleaning agent) dispenser will preferably dispense automatically if a hand is placed in front of the sensor, a foot pedal is pressed or it is voice activated. Low soap/disinfectant levels can be shown on a visual display or a series of LED lights and the status can be transmitted to a server as well as designated personnel who need to be notified. The visual display can be used to tell the individual washing his/her hands when compliance is achieved. Dispensers for gloves, masks and gowns also available (including dispensers for individual items as well as cabinet-type dispensers which track the removal of individual items). An inspection system can be employed to evaluate the quality of hand washing. FIG. 2 shows a soap/sanitizer dispenser 200 including an infrared sensor 210 to trigger cleaning agent delivery, a reservoir 220 to deliver a pre-measured aliquot of cleaning agent, a wireless Wi-Fi unit 230 to communicate with the monitor, a visual display 240 that indicates the status of the dispenser and whether hand washing compliance is attained and access cover 250 for replenishing of cleaning agents. A UV light source adjuvant hand sanitizer 260 can be activated when a cleaning agent is dispensed. A warning system will be activated by the motion detector if people enter or leave the room without using the dispenser or following other infection control precautions. A push button, a proximity sensor, a touch screen option, a verbal command, etc. can be used to inactivate the monitor system if the individual has washed his/her hands at the sink or has to enter room in an emergency. The monitor system will still continue to monitor/track all people entering and leaving the room or setting. The monitor unit can incorporate additional features in order to reduce or prevent infection due to portable medical instruments (tools) brought into a patient's room which are no longer clean due to previous use such as contact with other patients or improper handling. For example, stethoscopes, flashlights and other portable medical instruments brought into a patient's room are currently a means of spreading infection as they often carry Bacterium and/or viruses from other patients rooms. In one implementation the monitor unit capabilities could be expanded to contain a portal or insertion slot where a stethoscope or other portable medical instrument could be cleaned while the physician or nurse is within the patient's room. In another implementation a monitoring unit with tracking capabilities and this portable instrument-cleaning feature (and possibly cleaning capabilities for hands, etc.) could be stationed outside the patient's room. Therefore, in general, monitoring units (possibly with different features) can be located inside or outside a patient's room. A instrument such as a stethoscope could be inserted into a portal and have at least one of an UV light, an alcohol spray, a disinfectant spray or soap, etc. applied in order to clean the stethoscope. Prior to removal from the portal preferably any applied cleaning materials would be removed from the surface of the stethoscope (instrument). Tracking of portable medical instruments such as stethoscopes, with respect to use and cleaning, can be accomplished through a variety of means as previously described (RFIDs, video, bar codes, etc.).

Figure 3:
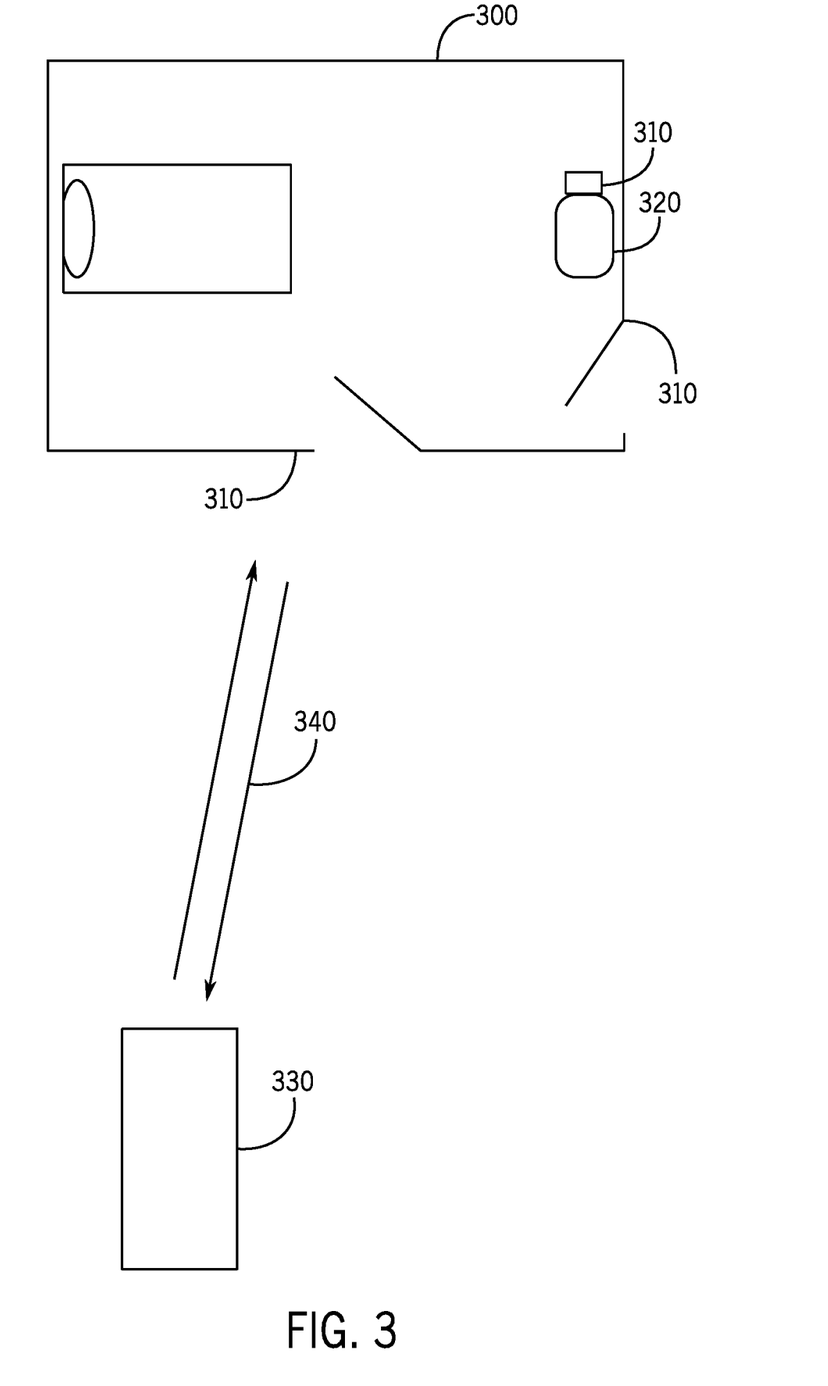
FIG. 3 illustrates schematically a floor plan of a monitored access room.

As shown in FIG. 3 a monitored room layout 300 includes monitor units with dispensers 310 located at both room entrances and next to the sink 320. All monitor units are linked by wired and/or wireless communications 340 to a central computer server 330. In one implementation of a monitoring system all hospital employees will be scanned for face detection. In addition, a physical profile can also be acquired. Hospital visitors will have images of their faces taken (and a physical profile can also be acquired) when they enter the hospital and are registered. Optionally additional identification techniques can be employed with hospital visitors. For example, hospital visitors can have their voices recorded for purposes of voice recognition. This can provide a level of redundancy in case the facial recognition system malfunctions or facial identification issues arise (visitors have a similar appearance, visitors must wear a mask, etc.) Alternatively, a hospital could decide to only use voice recognition identification if this results in an adequate level of compliance. Hospital visitors will be compliant and not spread infection within the hospital or from the hospital to community. Although the same identification techniques may be used with hospital employees as with hospital visitors additional or different identification techniques may be used with hospital employees. For example, hospital employees could also use additional biometric identification techniques as well as identification badges or bracelets with embedded RFIDs. Hospitals represent a high-profile application in which monitoring of hand washing and other infection control measures can have a major impact on the limiting the spread of diseases.

Numerous additional applications exist, including: health care clinics, corporations, cafeterias/lunchrooms, schools, government offices/agencies, public restrooms, restaurants, factories, the food preparation industry, stadiums, malls, airports, incarceration facilities, etc. In many cases monitors can be employed in both work areas and restrooms. It is relatively straightforward to register employees with a monitoring system as well as visitors with controlled access. For the case in which visitors or the public have controlled access to a facility such as a restroom the individual can be denied access unless he/she registers with the monitor which can record at least one of a face, a profile, a voice, etc. For the case of visitors or public access where no controlled registration is possible the monitoring system can record at least one of a face, a profile, a voice, etc. and inform the individual of the need to wash their hands prior to leaving a (for example) rest room. The computer system used with the monitoring unit can provide many capabilities in addition to establishing who enters and leaves a room (or setting), verification of hand washing (and other infection control or safety measures) and timing. The motion detector and video camera can be employed to verify both non-compliance as well as unauthorized entries (and thus can be linked to a security system including alerting security personnel and staff). For example, a RN assigned to a patient in a hospital can be alerted if an out-of-compliance person (e.g. family member) enters the patient's room and the nurse can return to reinforce the importance of compliance. The computer system can automatically email/text individual workers or infection control workers when protocols are breached or when pre-programmed threshold levels are crossed. Weekly, monthly, quarterly and yearly reports can be provided to employees regarding their level of compliance. High level authorized users (e.g. infection control officer, head of security, etc.) can access compiled data to target ways to improve compliance, reduce infection, improve security, etc. Furthermore, the accumulated monitoring data can be analyzed for tracking and modeling the spread of a disease (for example, within a hospital but also on a much larger scale such as public and/or private facilities within a community, a region, a state, a country).

The invention Literature references expressly incorporated by reference:

Tokhtuev Eugene, et al., Hand Hygiene Compliance Monitoring, U.S. Patent No. 2010/0315244 A1 [Dec. 16, 2010].

Sahud Andrew, Method and System to Monitor Hand Hygiene Compliance, U.S. Patent No. 2012/0055986 A1 [Mar. 8, 2012].

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. An infection control monitoring system comprising:
    at least one camera adapted for identifying and tracking individuals in a room for hygiene and safety compliance,
    a display adapted for interactive communications with the individuals in the room,
    an override device enabled by an authorized individual, wherein the monitoring system is programmed to accept electronic commands that override the monitoring system,
    an electronic communications link to a computer adapted for processing, storage, and verification of data acquired by the monitoring system, wherein the data is analyzed for infection control monitoring of the individuals in the room, and
    a dispenser unit adapted for dispensing a cleaning agent or infection control material, wherein the infection control monitoring system tracks compliance to a respective infection control step by the individuals in the room.

2. The infection control monitoring system of claim 1, further comprising at least one biometric identification device adapted for identifying the individuals in the room, the device selected from the list of:
    a camera adapted for face recognition and profile recognition of the individuals,
    a microphone adapted for voice recognition of the individuals,
    a biometric reader adapted for biometric recognition of the individuals,
    a badge reader adapted for identification of the individuals,
    an infrared imager adapted for infrared recognition of the individuals, and
    a chemical sensor adapted for chemical recognition of the individuals.

3. The infection control monitoring system of claim 1, wherein the dispenser unit comprises an insertion slot or portal for cleaning portable medical instruments, and wherein the infection control monitoring system is adapted for tracking of the cleaning of the portable medical instruments by registered individuals.

4. The infection control monitoring system of claim 3, further comprising a camera and a microphone adapted for registration of the registered individuals.

5. The infection control monitoring system of claim 1, wherein the override device comprises a push button, proximity sensor, microphone, touch screen, or virtual keyboard adapted to inactivate the system.

6. The infection control monitoring system of claim 1, wherein:
    the system is adapted to track compliance with use of infection control measures selected from masks, gowns, eye shields, head covers, overalls and hazmat suits; or
    the dispenser unit is adapted to track removal of items selected from gloves, masks and gowns.

7. The infection control monitoring system of claim 1, further comprising a sensor configured to sense presence of hands below the dispenser unit, wherein the dispenser unit is adapted to dispense soap or disinfectant.

8. The infection control monitoring system of claim 7, further comprising a clock programmed to appear on the display, wherein the system registers non-compliance to an aspect of infection control if the hands are removed prematurely to a time period.

9. The infection control monitoring system of claim 7, further comprising an inspection device adapted to examine the hands to evaluate washing effectiveness, wherein the infection control monitoring system is adapted to recognize an individual as compliant once the hands are washed.

10. The infection control monitoring system of claim 1, further comprising:
    an electronic locking mechanism communicating with the system via a wired or wireless network, wherein a door locks or unlocks based on the compliance; or
    a door opening mechanism linked to the system, wherein the door opening mechanism is adapted to automatically open a door based on the compliance.

11. The infection control monitoring system of claim 1, wherein the display is adapted to tell the individuals when the compliance is achieved.

12. An infection control monitoring method comprising:
    identifying and tracking individuals in a room for hygiene and safety compliance;
    interactively communicating with the individuals in the room;
    enabling an override device, wherein the monitoring system is programmed to accept electronic commands that override the monitoring system; and
    linking to a computer adapted for processing, storage, and verification of data acquired by the monitoring system, wherein the data is analyzed for monitoring the individuals in the room; and
    dispensing a cleaning agent or infection control material; and
    tracking compliance to a respective infection control step by the individuals in the room,
    sensing presence of hands below the dispenser unit, wherein the dispenser unit is adapted to dispense soap or disinfectant, and
    examining the hands to evaluate washing effectiveness, wherein the infection control monitoring system is adapted to recognize the individuals as compliant once the hands are washed; or programming a clock to appear on a display screen, wherein non-compliance is registered if the hands are removed prematurely to a time period.

13. The method of claim 12, further comprising suspending the infection control monitoring method with an authorized button or voice command.

14. The method of claim 12, further comprising communicating with the system via a wired or wireless network, wherein a door locks or unlocks based on the compliance, or a door automatically opens based on the compliance.

15. The method of claim 12, wherein the display screen further tell the individuals when compliance is achieved.

16. An infection control monitoring system comprising:
- at least one video camera adapted for identifying and tracking all individuals in a room space continuously throughout the room space for hygiene and safety compliance purposes,
- a display screen and a speaker adapted for interactive communications with the individuals in the room space,
- at least one non-contact override device, wherein the monitoring system is programmed to accept electronic commands that override the monitoring system and use of the at least one non-contact override device is limited to authorized individuals,
- an electronic communications link to a computer adapted for data post-processing, storage, verification and display of data acquired by the monitoring system, wherein the data is analyzed for monitoring the individuals in the room space, and
- a dispenser unit with an insertion slot or portal for cleaning portable medical instruments, and wherein the infection control monitoring system implements tracking of use and the cleaning of the portable medical instruments by registered individuals.

17. The infection control monitoring system of claim 16, further comprising at least one non-contact biometric identification device adapted for identifying all the individuals for tracking purposes, the device selected from the list of:
- a camera adapted for face recognition and profile recognition of the individuals,
- a microphone adapted for voice recognition of the individuals,
- a palm recognition biometric reader adapted for palm recognition of the individuals,
- an eye scanner adapted for the individuals to present an eye,
- a badge reader adapted for identification of the individuals,
- an infrared imager adapted for infrared recognition of the individuals, and
- a chemical sensor adapted for chemical recognition of the individuals.

18. The infection control monitoring system of claim 16, further comprising at least one of a video camera adapted for registration of the registered individuals and a microphone adapted for registration of the registered individuals.

19. The infection control monitoring system of claim 16, wherein the system is linked to a security system adapted for purposes of tracking at least one of: each individual throughout the room space, and the portable medical instruments throughout the room space.

20. The infection control monitoring system of claim 16, wherein the at least one video camera of the system is integrated with existing video cameras employed to monitor the room space.

21. The infection control monitoring system of claim 16, further comprising a sensor configured to sense presence of hands below the dispenser unit, wherein the dispenser unit is adapted to dispense soap or disinfectant, and
- an inspection device adapted to examine the hands to evaluate washing effectiveness, wherein the infection control monitoring system is adapted to recognize the individuals as compliant once the hands are washed; or
- a clock programmed to appear on the display screen, wherein the system registers non-compliance to an aspect of infection control if the hands are removed prematurely to a time period.

22. The infection control monitoring system of claim 16, further comprising:
- an electronic locking mechanism communicating with the system via a wired or wireless network, wherein a door locks or unlocks based on the compliance, or
- a door opening mechanism linked to the system, wherein the door opening mechanism is adapted to automatically open a door based on the compliance.

* * * * *